(12) United States Patent
Ooi et al.

(10) Patent No.: US 10,302,555 B2
(45) Date of Patent: May 28, 2019

(54) SENSOR FOR AND METHOD OF SENSING AN ANALYTE, AND METHOD OF FABRICATING A SENSOR

(71) Applicant: Agency for Science, Technology and Research, Singapore (SG)

(72) Inventors: Zi En Ooi, Singapore (SG); Jie Zhang, Singapore (SG); Kok Leong Chang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/577,603

(22) PCT Filed: May 27, 2016

(86) PCT No.: PCT/SG2016/050252
§ 371 (c)(1),
(2) Date: Nov. 28, 2017

(87) PCT Pub. No.: WO2016/195595
PCT Pub. Date: Dec. 8, 2016

(65) Prior Publication Data
US 2018/0136117 A1 May 17, 2018

(30) Foreign Application Priority Data
May 29, 2015 (SG) .............. 10201504262V (51) Int. Cl.
*G01N 21/25* (2006.01)
*G01N 21/27* (2006.01)
(Continued)

(52) U.S. Cl.
CPC ............. *G01N 21/27* (2013.01); *G01N 21/78* (2013.01); *G01N 21/80* (2013.01)

(58) Field of Classification Search
CPC ........ G01J 3/26; G01J 3/02; G01J 3/51; G01J 9/00; G01N 21/255
(Continued)

(56) References Cited

U.S. PATENT DOCUMENTS

| 5,315,673 A | 5/1994 | Stetter et al. |
| 2014/0377879 A1 | 12/2014 | Sharrock et al. |

FOREIGN PATENT DOCUMENTS

| WO | 2012125494 A2 | 9/2012 |
| WO | 2015033229 A2 | 3/2015 |

OTHER PUBLICATIONS

International Preliminary Report on Patentability for International Application No. PCT/SG2016/050252 dated Dec. 5, 2017, pp. 1-6.
(Continued)

*Primary Examiner* — Md M Rahman
(74) *Attorney, Agent, or Firm* — Winstead, P.C.

(57) ABSTRACT

The invention relates to a sensor for sensing an analyte. The sensor comprises a detection sensing element having an electrical property variable with the amount of optical light received by the detection sensing element, a control sensing element having an electrical property variable with the amount of optical light received by the control sensing element, a detection optical element for contacting an analyte and transmitting a first amount of optical light received thereby to the detection sensing element in response to the contact with the analyte, a control optical element for contacting a control medium and transmitting a second amount of optical light received thereby to the control sensing element in response to the contact with the control medium, and an output arrangement configured to provide an indication based on the electrical property of the detection sensing element when the first amount of optical light is received by the detection sensing element, with respect to the electrical property of the control sensing element when
(Continued)

the second amount of optical light is received by the control sensing element, thereby sensing said analyte. In various embodiments, the sensor is a pH sensor and electrical resistance is the electrical property variable in response to the amount of optical light received by the sensing elements.

16 Claims, 8 Drawing Sheets

(51) Int. Cl.
    *G01N 21/78*    (2006.01)
    *G01N 21/80*    (2006.01)
(58) Field of Classification Search
    USPC .......................................................... 356/416
    See application file for complete search history.

(56) References Cited

OTHER PUBLICATIONS

Written Opinion of the International Searching Authority for International Application No. PCT/SG2016/050252 dated Jul. 25, 2016, pp. 1-4.

- provide a detection sensing element — 602
- provide a control sensing element — 604
- contact a detection optical element with the analyte — 606
- contact a control optical element with a control medium — 608
- provide optical light to the detection optical element and the control optical element — 610
- sense said analyte by providing an indication — 612

| LED intensity (relative to ~1 sun) | Photoconductors without PANI filter | | | Photoconductors with PANI filter | | |
| --- | --- | --- | --- | --- | --- | --- |
| | Test resistance (MΩ) | Control resistance (MΩ) | Resistance ratio | Test resistance (MΩ) (Blue, pH9) | Control resistance (MΩ) (Green, neutral) | Resistance ratio |
| 0.12 | 1.48 | 1.37 | 1.08 | 3.10 | 2.09 | 1.48 |
| 0.099 | 1.63 | 1.63 | 1.00 | 3.22 | 2.35 | 1.37 |
| 0.085 | 1.79 | 1.72 | 1.04 | 3.46 | 2.63 | 1.32 |
| 0.071 | 1.97 | 1.96 | 1.01 | 3.75 | 2.87 | 1.31 |
| 0.057 | 2.28 | 2.21 | 1.03 | 3.92 | 3.05 | 1.29 |
| 0.034 | 2.87 | 2.75 | 1.04 | 4.56 | 3.73 | 1.22 |

SENSOR FOR AND METHOD OF SENSING AN ANALYTE, AND METHOD OF FABRICATING A SENSOR

CROSS-REFERENCE TO RELATED APPLICATION

This application claims the benefit of priority of Singapore application No. 10201504262V filed on May 29, 2015, the contents of it being hereby incorporated by reference in its entirety for all purposes.

TECHNICAL FIELD

Various aspects of this disclosure relate to sensors for sensing analytes, methods of sensing analytes, and methods of fabricating sensors for sensing analytes.

BACKGROUND

There are many existing materials that exhibit a change in optical transmittance (e.g. colour) in response to an analyte, such as via ion concentration or gases. Optical spectrometry is an accurate method of quantifying the amount of analyte present. However, this is an expensive and non-portable method.

SUMMARY

Various embodiments may provide a sensor for sensing an analyte. The sensor may include a detection sensing element having an electrical property variable with the amount of optical light received by the detection sensing element. The sensor may also include a control sensing element having an electrical property variable with the amount of optical light received by the control sensing element. The sensor may additionally include a detection optical element for contacting the analyte. The detection optical element may be configured to transmit a first amount of optical light received by the detection optical element to the detection sensing element when the detection optical element is in contact with the analyte. The sensor may also include a control optical element for contacting a control medium. The control optical element may be configured to transmit a second amount of optical light received by the control optical element to the control sensing element when the control optical element is in contact with the control medium. The sensor may additionally include an output arrangement configured to provide an indication based on the electrical property of the detection sensing element when the first amount of optical light is received by the detection sensing element, with respect to the electrical property of the control sensing element when the second amount of optical light is received by the control sensing element, thereby sensing said analyte.

Various embodiments may provide a method of sensing an analyte. The method may include providing a detection sensing element having an electrical property variable with the amount of optical light received by the detection sensing element. The method may also include providing a control sensing element having an electrical property variable with the amount of optical light received by the control sensing element. The method may also include contacting a detection optical element with the analyte. The detection optical element may be configured to transmit a first amount of optical light received by the detection optical element to the detection sensing element when the detection optical element is in contact with the analyte. The method may additionally include contacting a control optical element with a control medium, said control optical element configured to transmit a second amount of optical light received by the control optical element to the control sensing element when the control optical element is in contact with the control medium. The method may further include providing optical light to the detection optical element and the control optical element so that the detection optical element transmits the first amount of optical light to the detection sensing element and the control optical element transmits the second amount of optical light to the control sensing element. The method may further include sensing said analyte based on an indication, the indication based on the electrical property of the detection sensing element when the first amount of optical light is received by the detection sensing element, with respect to the electrical property of the control sensing element when the second amount of optical light is received by the control sensing element.

Various embodiments may provide a method of fabricating a sensor for sensing analyte. The method may include providing a detection sensing element having an electrical property variable with the amount of optical light received by the detection sensing element. The method may include providing a control sensing element having an electrical property variable with the amount of optical light received by the control sensing element. The method may also include providing a detection optical element for contacting the analyte, said detection optical element configured to transmit a first amount of optical light received by the detection optical element to the detection sensing element when the detection optical element is in contact with the analyte. The method may further include providing a control optical element for contacting a control medium, said control optical element configured to transmit a second amount of optical light received by the control optical element to the control sensing element when the control optical element is in contact with the control medium. The method may include providing a output arrangement configured to provide an indication based on the electrical property of the detection sensing element when the first amount of optical light is received by the detection sensing element, with respect to the electrical property of the control sensing element when the second amount of optical light is received by the control sensing element, thereby sensing said analyte.

BRIEF DESCRIPTION OF THE DRAWINGS

The invention will be better understood with reference to the detailed description when considered in conjunction with the non-limiting examples and the accompanying drawings, in which.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

A first layer over a second layer may refer to the first layer on the second layer or that the first layer is separated from the second layer by one or more intervening layers. The first layer on the second layer may refer to the first layer is in contact with the second layer.

Various embodiments may seek to provide a cheaper and/or more portable solution.

Figure 1:
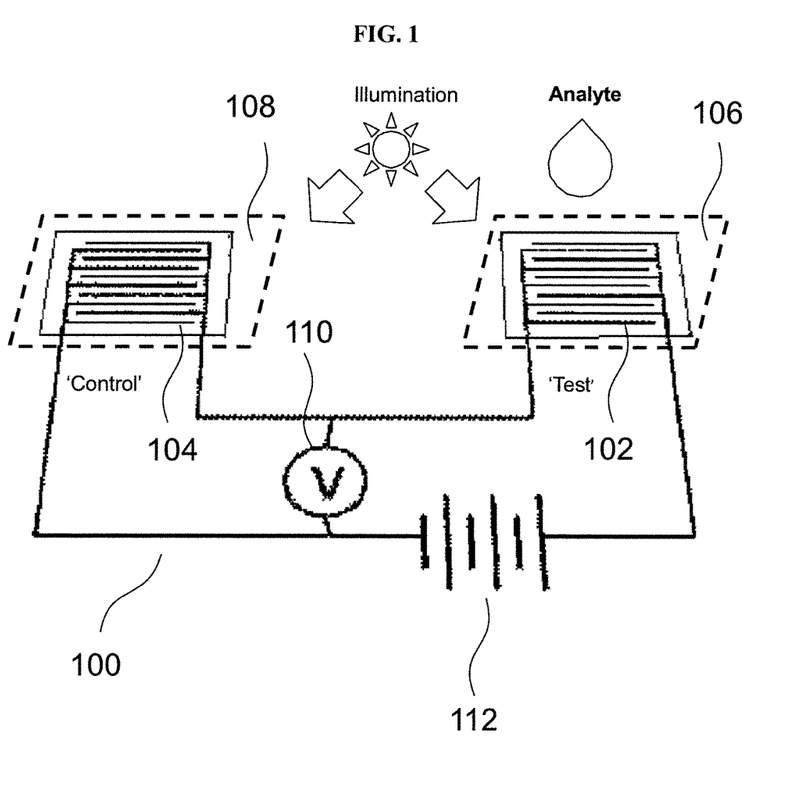
FIG. 1 is a schematic illustrating a sensor according to various embodiments.

FIG. 1 is a schematic illustrating a sensor 100 according to various embodiments. The sensor 100 may include a detection sensing element 102 having an electrical property variable with optical light received by the detection sensing element 102. The detection sensing element 102 may include a detection photoconductor, which may be an organic photoconductor. The detection sensing element 102 may include a pair of interdigitated electrodes. The pair of interdigitated electrodes may be spaced or separated apart from each other. The detection sensing element 102 may further include a coating of organic photoconductive material over the pair of interdigitated electrodes. The organic photoconductive material may be a bulk heterojunction blend used for solar cell applications.

The sensor 100 may include a control sensing element 104 having an electrical property variable with optical light received by the control sensing element 104. The control sensing element 104 may include a control photoconductor, which may be an organic photoconductor. The control sensing element 104 may include a pair of interdigitated electrodes. The pair of interdigitated electrodes may be spaced or separated apart from each other. The control sensing element 104 may further include a coating of organic photoconductive material over the pair of interdigitated electrodes. The organic photoconductive material may be a bulk heterojunction blend used for solar cell applications.

As shown in FIG. 1, the detection sensing element 102 and the control sensing element 104 may be connected in series. A first end of the detection sensing element 102 may be connected to a first end of the control sensing element 104. A second end of the detection sensing element 102 may be connected to a first end of a fixed voltage source 112, such as an alkaline battery. The fixed voltage source 112 may alternatively be referred to as a drive voltage source. The voltage source 112 may be configured to provide a drive voltage, which may alternatively be referred to as a supply voltage. A second end of the control sensing element 104 may be connected to a second end of the fixed voltage source 112. In other words, the voltage source 112 may be in electrical connection with the detection sensing element 102 and the control sensing element 104. A first interdigitated electrode of the detection sensing element 102 may be connected to a first interdigitated electrode of the control sensing element 104. A second interdigitated electrode of the detection sensing element 102 may be connected to a first end of the voltage source 112. A second interdigitated electrode of the control sensing element 104 may be connected to a second end of the voltage source 112.

The detection sensing element 102, the control sensing element 104, and the drive voltage source 112 may form a circuit arrangement. The circuit arrangement or sensor 100 may further include an output arrangement 110, such as a readout voltage device shown in FIG. 1.

The voltage source 112 may be configured to generate a voltage potential at a node between the detection sensing element 102 and the control sensing element 104. The readout voltage device 110 may be configured to measure or provide the voltage potential of the node. A first end of the readout voltage device 110 may be connected to the node, and a second end of the readout voltage device 110 may be connected to a first end or a second end of the voltage source 112. The readout voltage device may be configured to read or provide a potential difference between the node, and the first end or the second end of the readout voltage device 110.

Due to the high resistance of the detection sensing element 102 and the control sensing element 104, the sensor 100 or the circuit arrangement may draw very little power, especially if the sensor 100 or the circuit arrangement is kept in the dark.

The sensor 100 may further include a detection optical element 106. The sensor 100 may also include a control optical element 108. In various embodiments, the detection optical element 106 may be a first portion of a colour filter and the control optical element 108 may be a second portion of the colour filter. In other words, the detection optical element 106 and the control optical element 108 may be different parts or portions of a continuous optical element, such as a colour filter.

In various other embodiments, the detection optical element 106 and the control optical element 108 may be separate elements.

In various embodiments, the detection optical element 106 may be configured to change an optical property, such as optical transmittance or optical absorbance, when the detection optical element 106 is in contact with different media. In various embodiments, the control optical element 108 may be configured to change an optical property, such as optical transmittance or optical absorbance, when the control optical element 108 is in contact with different media. In various embodiments, the colour filter may be configured to change an optical property, such as optical transmittance or optical absorbance, when the control optical element is in contact with different media.

In various embodiments, the colour filter may be configured to change colour when the colour filter is in contact with different media. The colour filter may change colour when the colour filter is in contact with an analyte.

In various embodiments, the detection optical element 106 (or the control optical element 108) may be configured to change an optical property based on or due to a property of the medium or environment the detection optical element 106 (or the control optical element 108) is in contact with.

The property of the medium may be a chemical property, a biological property or a physical property. A chemical property may include pH of the medium or the environment, ion concentration of the medium or the environment etc. A biological property may include presence of a specific biomolecule in the medium or the environment. A physical property may include temperature, moisture, pressure, stress or strain of the medium or the environment.

The detection sensing element 102 may have an electrical property, e.g. electrical resistance, variable with optical light received by the detection sensing element 102. The resistance of the detection sensing element 102 may change in response to the amount of optical light received by the detection sensing element 102. The control sensing element 104 may have an electrical property, e.g. electrical resistance, variable with optical light received by the control sensing element 104. The resistance of the control sensing element 104 may change in response to the amount of optical light received by the control sensing element.

Before use or operation, the detection sensing element 102 and the control sensing element 104 may have substantially the same resistance. Both the detection optical element 106 and the control optical element 108 may be in contact with a control medium such as air or a buffer solution. As neither the detection optical element 106 nor the control optical element 108 are not in contact with the analyte, substantially the same amount of optical light may pass through the detection optical element 106 and the control optical element 108 to the detection sensing element 102 and the control sensing element 104 respectively. As such, regardless of the lighting conditions, both the detection sensing element 102 and the control sensing element 104 may have substantially the same resistance. The potential difference across each of the detection sensing element 102 and the control sensing element 104 may be about half of the source voltage provided by the voltage source 112. The potential of the node may be half of the source voltage.

The half portion of the filter over the detection sensing element 102 (labeled as 'Test'), i.e. the detection optical element 106, may be exposed or may be in contact with the target analyte to be sensed. The other half portion of the filer over the control sensing element 104, i.e. the control optical element 108, may not be exposed to the target analyte. In other words, the other half portion of the filer over the control sensing element 104 may be isolated from the analyte. The other half portion of the filer over the control sensing element 104 may be exposed to a control medium, such as vacuum, air, or a buffer solution.

When the detection optical element 106 is in contact with the analyte and the control optical element 108 is isolated from the analyte, the amount of optical light transmitted by the detection optical element 106 to the detection sensing element 102, and the amount of optical light transmitted by the control optical element 108 to the control sensing element 104 may be different. The difference in the amount of optical light received by the detection optical element 106 and the control optical element 108 may result in the resistance of the detection sensing element 102 to be different from the resistance of the control sensing element 104. The detection sensing element 102 and the control sensing element 104 may behave as an imbalance voltage divider, and the voltage potential or the voltage difference at the node may change, thus sensing the analyte.

In various embodiments, the potential of the node between the detection sensing element 102 and the control sensing element 104 may be adjusted by adjusting the voltage source 112 or the supply voltage or drive voltage provided by the voltage source 112. The potential of the node may be proportional to the supply voltage or drive voltage provided by the voltage source 112. The sensitivity of the sensor 100 may be increased by increasing the drive voltage. A large voltage output may be more readable for a (separate) printed readout circuit.

The potential at the node between the detection sensing element 102 and the control sensing element 104 may be adjusted by adjusting the relative (initial) resistances of the detection sensing element 102 and the control sensing element 104, e.g. by changing the initial resistance of the detection sensing element 102 while maintaining the initial resistance of the control sensing element 104. The relative (initial) resistances may be adjusted by adjusting the relative dimensions of the detection sensing element 102 and the control sensing element 104. The initial resistance of a sensing element may refer to the resistance of the sensing element before the sensing element is used in operation.

In other words, the ratio of the potential difference across the detection sensing element 102 and the potential difference across the control sensing element 104 may be adjusted. In various embodiments, the potential difference across the detection sensing element 102 and the potential difference across the control sensing element 104 may be set to be different before operation, i.e. when the detection optical element 106 and the control optical element 108 are in contact with a common medium. When the detection sensing element 102 is in contact with the analyte while the control optical element 108 is in contact with a contact medium, the change in potential difference (e.g. increase in potential difference) across the detection sensing element 102 may be different, e.g. may be greater, than the change in potential difference across the control sensing element 104, which may cause the potential of the node to change. In other words, the difference in relative change of potential differences across the detection sensing element 102 and across the control sensing element may lead to a change in the potential of the node. Adjusting the ratio may be due to signal-to-noise (SNR) requirements.

In embodiments wherein the initial resistance of the detection sensing element 102 is already different from the initial resistance of the control sensing element 104 before operation, the ratio of the resistance of the detection sensing element 102 to the resistance of the control sensing element 104 may change from the initial ratio (i.e. of the initial resistance of the detection sensing element 102 to the initial resistance of the control sensing element 104) to a new ratio when the detection optical element 106 is exposed to the analyte, while the control optical element 108 is isolated from the analyte. In other words, the ratio of the resistance of the detection sensing element 102 to the resistance of the control sensing element 104 may change between when the detection sensing element 102 is not in contact with the analyte, and when the detection sensing element 102 is in contact with the analyte. The voltage at the node may change due to a change in ratio of the resistance of the detection sensing element 102 to the resistance of the control sensing element 104.

In various embodiments, the analyte and the colour filter may be electrically insulated from the detection sensing element 102 and the control sensing element 104, or the circuit arrangement, so no limit on the driving voltage may be required.

In various embodiments, one or more of the interdigitated electrodes, the organic photoconductive material, and the colour filter, may be printed on or over a substrate. The technology for printing may already exist.

In various embodiments, the resistance of the sensor 100 may be very high, thus drawing very little power.

In various embodiments, the colour filter may be selected to sense a desired target analyte.

In various embodiments, the colour filter may include polyaniline (PANI). In various embodiments, the detection optical element 106 may include polyaniline. In various embodiments, the control optical element 108 may include polyaniline.

Polyaniline is a polymer that may change colour in response to pH. The analyte and the control medium may have different pH.

Figure 2:
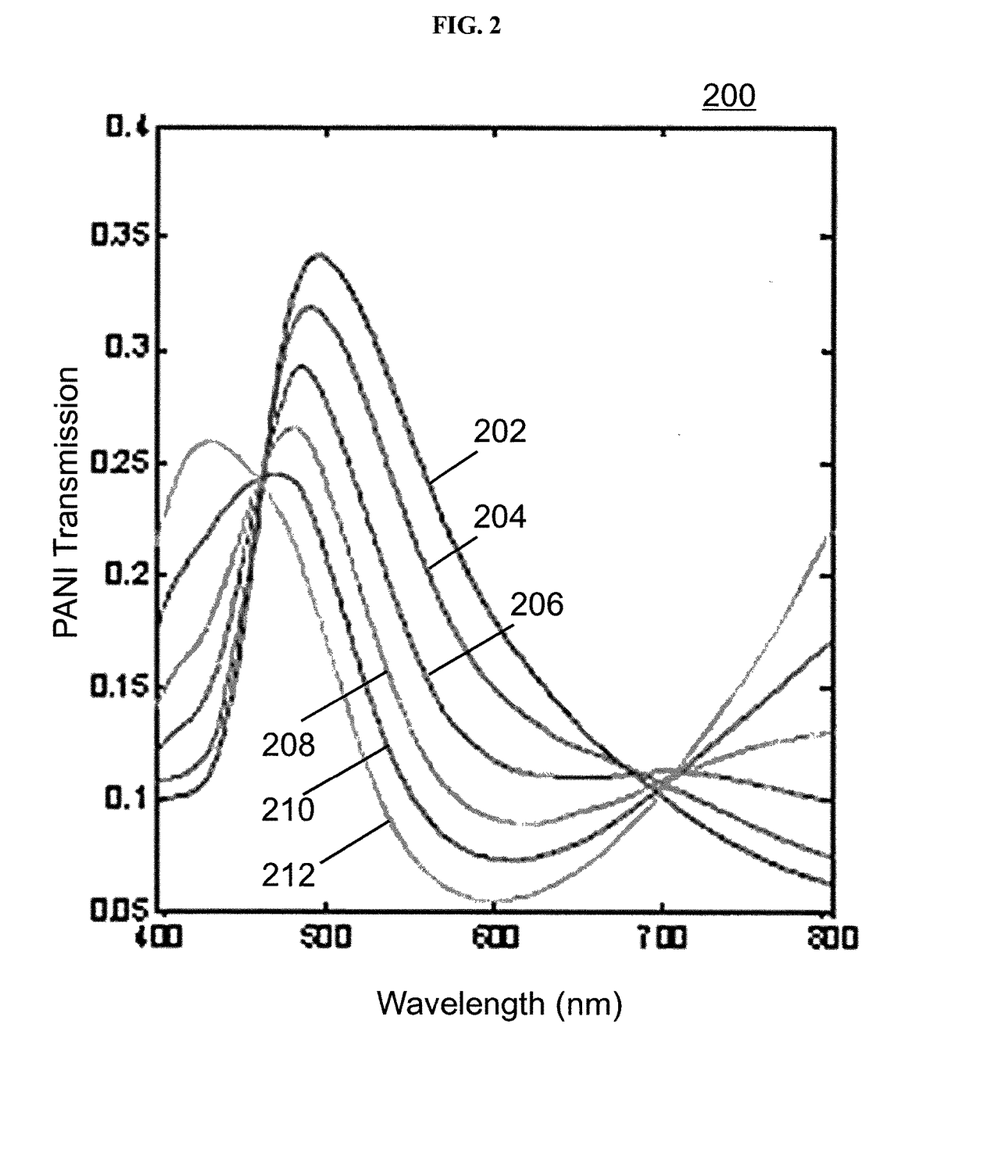
FIG. 2 is a plot of transmission of polyaniline (PANT) (in arbitrary unit or a.u.) as a function of wavelength (in nanometer or nm) illustrating the transmission spectra of a polyaniline film at various pH values according to various embodiments.

FIG. 2 is a plot 200 of transmission of polyaniline (PANI) (in arbitrary unit or a.u.) as a function of wavelength (in nanometer or nm) illustrating the transmission spectra of a polyaniline film at various pH values according to various embodiments. 202 shows the data in a medium of pH 6; 204 shows the data in a medium of pH 6.5; 206 shows the data in a medium of pH 7; 208 shows the data in a medium of pH 7.5; 210 shows the data in a medium of pH 8; and 212 shows the data in a medium of pH 9.

Figure 3:
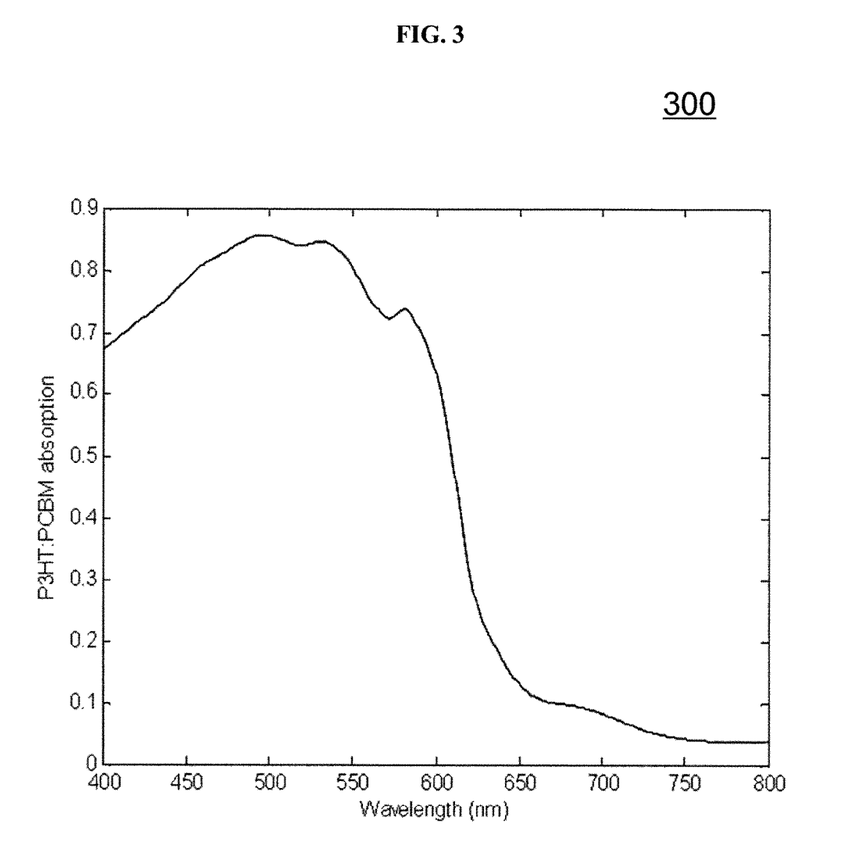
FIG. 3 is a plot of the absorption of poly (3-hexylthiophene):phenyl-C61—butyric acid methyl ester (P3HT: PCBM) (in arbitrary unit or a.u.) as a function of wavelength (in nanometer or nm) illustrating the optical absorption spectrum of poly (3-hexylthiophene):phenyl-C61—butyric acid methyl ester (P3HT: PCBM).

In various embodiments, the organic photoconductive material may be poly (3-hexylthiophene):phenyl-C61—butyric acid methyl ester (P3HT: PCBM). FIG. 3 is a plot 300 of the absorption of poly (3-hexylthiophene):phenyl-C61—butyric acid methyl ester (P3HT: PCBM) (in arbitrary unit or a.u.) as a function of wavelength (in nanometer or nm) illustrating the optical absorption spectrum of poly (3-hexylthiophene):phenyl-C61—butyric acid methyl ester (P3HT: PCBM).

The sensor may be a pH sensor. Based on FIGS. 2 and 3, a pH sensor based on the pH dependent colour of PANI, and the photoconductive effect of P3HT: PCBM may be simulated. The goal is to simulate the resistance balance effect.

The conductivity σ of each photoconductor is proportional to the square root of the light absorbed by P3HT: PCBM as provided in Equation (1):

$$\sigma \propto \text{charge carrier density} \propto \sqrt{\text{lightabsorbed}} \quad (1)$$

The amount of light absorbed may in turn be proportional to the amount of light available, PANI transmission, and absorption by P3HT: PCBM as provided in Equation (2):

$$\# \text{ of photons absorbed} \propto \int P(\lambda)T_{PANI}(\lambda)A_{P3HT}(\lambda)d\lambda \quad (2)$$

where $T_{PANI}$ is the transmission through PANI, $A_{P3HT}$ is the absorption of P3HT:PCBM and P is the incident light intensity. $T_{PANI}$, $A_{P3HT}$, and P are dependent on the wavelength of light λ.

$$\text{Therefore, } \sigma \propto \sqrt{\int P(\lambda)T_{PANI}(\lambda)A_{P3HT}(\lambda)d\lambda} \quad (3)$$

The conductivity ratio between the two photoconductors may be provided by:

$$\frac{\sigma_{test}(pH)}{\sigma_{control}} = \sqrt{\frac{\int P(\lambda)T_{PANI}(\lambda, pH)A_{P3HT}(\lambda)d\lambda}{\int P(\lambda)T_{PANI}(\lambda)A_{P3HT}(\lambda)d\lambda}} \quad (4)$$

where one of the two PANI filters, changes optical transmission in response to a pH change (as indicated by $T_{PANI}(\lambda,pH)$). $\sigma_{test}$ represents the conductivity of the photoconductor receiving the optical light transmitted through the PANI filter which changes optical transmittance in response to a change in pH, and $\sigma_{control}$ represents the conductivity of the photoconductor receiving optical light transmitted through the other PANI filter which does not have a change in optical transmissivity. The resistance ratio may be taken as the inverse of the conductivity ratio.

Figure 4:
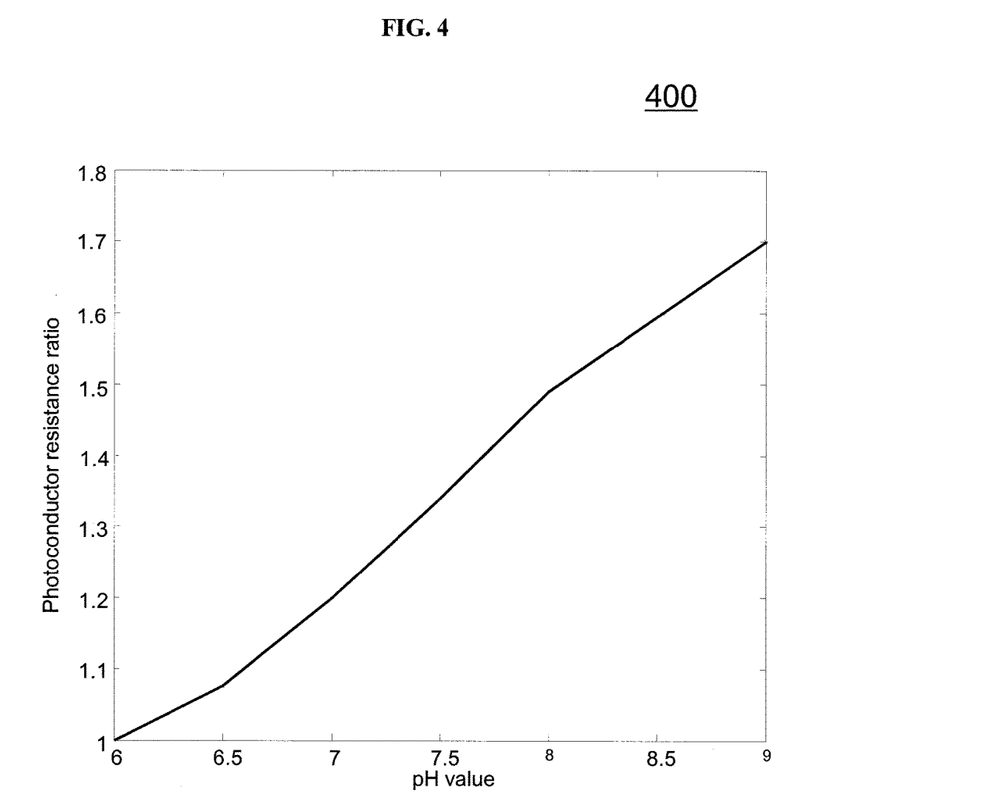
FIG. 4 is a plot of photoconductor resistance ratio as a function of pH value according to various embodiments.

FIG. 4 is a plot 400 of photoconductor resistance ratio as a function of pH value according to various embodiments.

The voltage to be read from the sensor, i.e. the voltage at the node between the two photoconductors may be provided by V readout in Equation (5).

$$V_{readout} = \frac{V_{drive}}{1 + (\text{resistance ratio})} \quad (5)$$

For a 9V battery source, the estimated voltage expected (at the node) at pH=6 may be 4.5V, and the voltage may be expected to change to 3.3V when the pH is 9.

Figure 5:
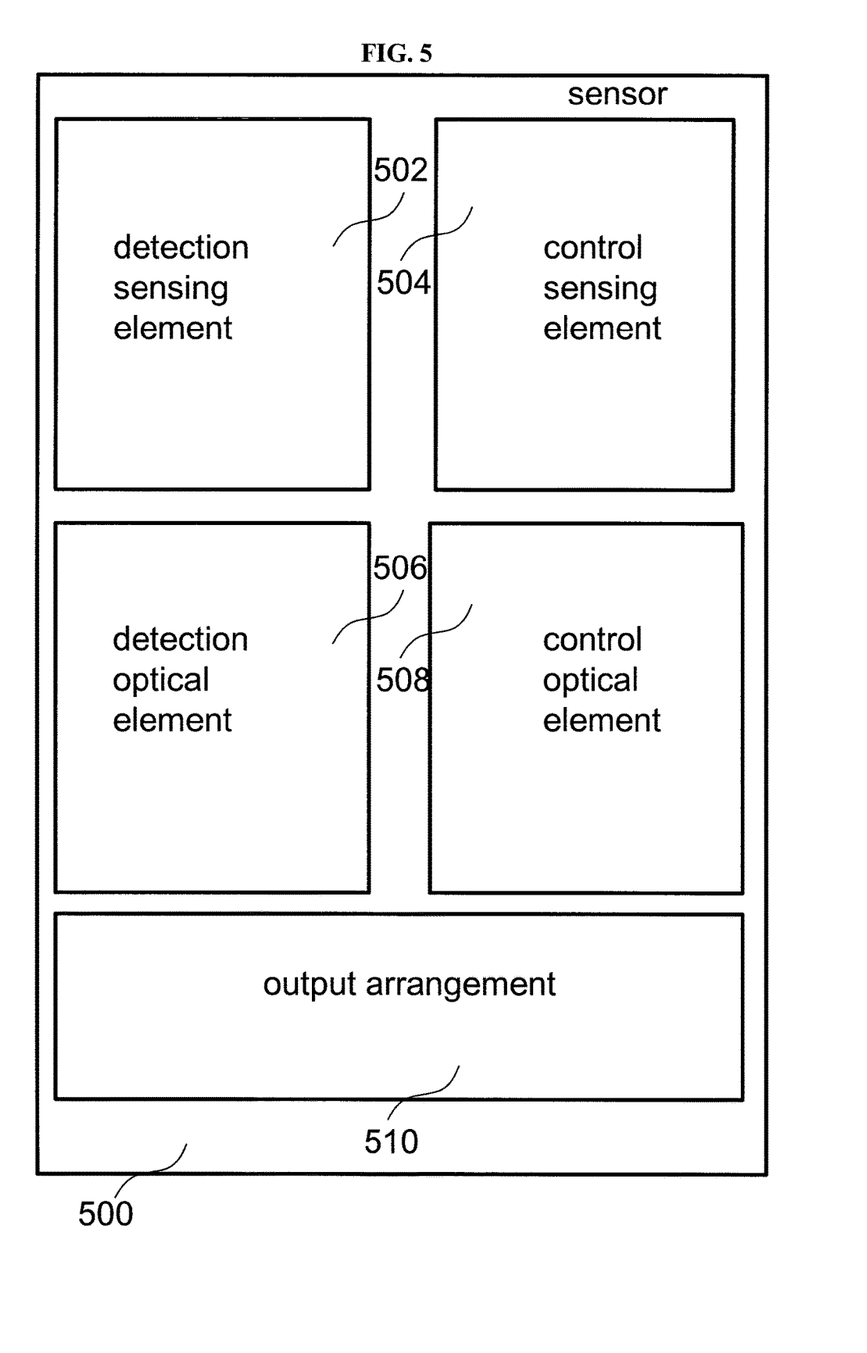
FIG. 5 is a schematic illustrating a sensor for sensing an analyte according to various embodiments.

FIG. 5 is a schematic illustrating a sensor 500 for sensing an analyte according to various embodiments. The sensor 500 may include a detection sensing element 502 having an electrical property variable with the amount of optical light received by the detection sensing element 502. The sensor 500 may also include a control sensing element 504 having an electrical property variable with the amount of optical light received by the control sensing element 504. The sensor 500 may additionally include a detection optical element 506 for contacting the analyte. The detection optical element 506 may be configured to transmit a first amount of optical light received by the detection optical element 506 to the detection sensing element 502 when the detection optical element 506 is in contact with the analyte. The sensor 500 may also include a control optical element 508 for contacting a control medium. The control optical element 508 may be configured to transmit a second amount of optical light received by the control optical element 508 to the control sensing element 504 when the control optical element 508 is in contact with the control medium. The sensor 500 may additionally include a output arrangement 510 configured to provide an indication based on the electrical property of the detection sensing element when the first amount of optical light is received by the detection sensing element 502, with respect to the electrical property of the control sensing element when the second amount of optical light is received by the control sensing element 504, thereby sensing said analyte.

In other words, the sensor may include a pair of sensing elements 502, 504, with an electrical property that changes with the amount of optical light that are incident on the sensing elements. Optical elements 506, 508 transmit optical light to the sensing elements. One optical element, such as a portion of a colour filter, may transmit optical light to a single sensing element. The optical elements 506, 508 have an optical property that changes the transmission of optical light through the optical elements based on the medium or environment that the optical elements 506, 508 are in contact with. One of the optical elements 506, such as a portion of a colour filter, may contact an analyte and transmit a first amount of optical light to a first sensing element 502, while the other optical element 508, such as another portion of the colour filter may be in contact with a control medium and transmit a second amount of optical light to the second sensing element 504. An output arrangement 510 may be used to provide an indication on the relative change in a value of the electrical property of the first sensing element 502, and a value of the electrical property of the second sensing element 504.

In various embodiments, the detection optical element 506 may be configured to transmit a first amount of optical light received by the detection optical element 506 to the detection sensing element 502 upon contact of the detection optical element 506 with the analyte, i.e. when the detection optical element 506 is in contact with the analyte. The control optical element 508 may be configured to transmit a second amount of optical light received by the control optical element 508 to the control sensing element 504 upon contact of the control optical element 508 with the control medium, i.e. when the control optical element 508 is in contact with the control medium. The sensor 500 may additionally include an output arrangement 510 configured to provide an indication based on the electrical property of the detection sensing element upon receiving the first amount of optical light by the detection sensing element 502, and further based on the electrical property of the control sensing element upon receiving the second amount of optical light by the control sensing element 504, thereby sensing said analyte.

The first amount of optical light may be different from the second amount of optical light. The first amount of optical light and the second amount of optical light may be determined relative to an equal amount of optical light incident or received by each of the detection optical element 506 and the control optical element 508. When the detection optical element 506 are not in contact with the analyte, i.e. when both the optical sensing element 506 and the control sensing element 508 are in contact with a common medium such as a control medium, e.g. air or a buffer solution, and an equal amount of light is incident or received by each of the detection optical element 506 and the control optical element 508, the detection optical element 506 may transmit an amount of light (to the detection sensing element 502) substantially equal to an amount of light transmitted by the control optical element 508 (to the control sensing element 504). When the detection optical element 506 is in contact with a target analyte while the control detection element 508 is in contact with a control medium having a property (e.g. pH, ion concentration etc.) different from the target analyte, and when the amount of optical light incident or received by each of the detection optical element 506 and the control optical element 508 is substantially equal, the amount of optical light transmitted by the detection optical element 506 may be different from the amount of optical light transmitted by the control optical element 508.

In various embodiments, the amount of light transmitted by the detection optical element 506 (or the control optical element 508) may refer to the proportion of optical light received by the detection optical element 506 (or the control optical element 508) that is transmitted by the detection optical element 506 (or the control optical element 508). In other words, the amount of light transmitted by the detection optical element 506 (or the control optical element 508) may refer to the amount of light transmitted by the detection optical element 506 (or the control optical element 508) per unit of optical light received by the detection optical element 506 (or the control optical element 508). When the detection optical element 506 is not in contact with the analyte, i.e. when both the optical sensing element 506 and the control sensing element 508 are in contact with a common medium such as a control medium, e.g. air or a buffer solution, and an unequal amount of light is incident or received by each of the detection optical element 506 and the control optical element 508 (e.g. due to different optical sources being used to provide optical light to the detection optical element 506 and the control optical element 508, or different distances between a common optical source to the detection optical element 506 and the control optical element 508, or due to a difference in structure between the detection optical element 506 and the control optical element 508 etc.), the amount of light transmitted by the detection optical element 506 may not be equal to the amount of light transmitted by the control optical element 508, although the proportion of optical light transmitted by the detection optical element 506 may be substantially equal to the proportion of optical light transmitted by the control optical element 508. When the detection optical sensing element 506 is in contact with the analyte while the control optical sensing element 508 is in contact with a control medium, the proportion of optical light transmitted by the detection optical element 506 may be different from the proportion of optical light transmitted by the control optical element 508. The indication provided by the output arrangement 510 may be based on the proportion of optical light transmitted by the detection optical element 506, with respect to the proportion of optical light transmitted by the control optical element 508.

In various embodiments, the electrical property may be electrical resistance or electrical conductance. In various embodiments, the electrical property of the detection sensing element 502 may be or may refer to a resistance of the detection sensing element 502, while the electrical property of the control sensing element 504 may be or may refer to a resistance of the control sensing element 504. In various embodiments, the electrical property of the detection sensing element 502 may be or may refer to a conductance of the detection sensing element 502, while the electrical property of the control sensing element 504 may be or may refer to a conductance of the control sensing element 504.

In various embodiments, the detection sensing element 502 and the control sensing element 504 may be connected in series. The sensor 500 may further include a voltage source in electrical connection with the detection sensing element 502 and the control sensing element 504. The voltage source may be configured to provide a supply voltage. The voltage source may be configured to generate a voltage potential at a node between the detection sensing element 502 and the control sensing element 504.

The output arrangement 510 may be or may include a voltage readout device configured to read the voltage potential of the node. The indication may be an output signal such as the voltage potential of the node.

In various embodiments, the sensor or the circuit arrangement may be configured such that a maximum range of the output signal is proportional to the supply voltage of the power source. The maximum range of the output signal may be substantially the same as the supply voltage.

In various other embodiments, the detection sensing element 502 and the control sensing element 504 may be connected in parallel. The sensor 500 may further include a current source in electrical connection with the detection sensing element and the control sensing element.

The output arrangement 510 may include a first current readout device connected in series to the detection sensing element 502 and a second current readout device connected in series to the control sensing element 504.

A first end of the detection sensing element 502 may be connected to a first end of the first current readout device, and a first end of the control sensing element 504 may be connected to a first end of the second current readout device. A second end of the detection sensing device 502 and a second end of the control sensing device 504 may be connected to a first end of the current source. A second end of the first current readout device and a second end of the second current readout device may be connected to a second end of the current source.

The indication may be based on a first output signal from the first current readout device, which indicates a first output current flowing through the detection sensing device 502, with respect to a second output signal from the second current readout device, which indicates a second output current flowing through the control sensing device 504. The first output signal is based on the electrical property of the detection sensing element 502 when the first amount of optical light is received by the detection sensing element 502, and the second output signal is based on the electrical property of the control sensing element 504 when the second amount of optical light is received by the control sensing element 504.

In various embodiments, the sensor or the circuit arrangement may be configured such that a maximum range of the first output signal is proportional to the supply current of the current source. The maximum range of the output signal may be substantially the same as the supply current provided by the current source.

In various embodiments, the detection optical element 506 may be a first portion of a colour filter and the control optical element 508 may be a second portion of the colour filter. The first portion of the colour filter may cover the detection sensing element 502 and the second portion of the colour filter may cover the control sensing element 504. The detection optical element 506 and the control optical element 508 may be different portions of a single optical structure, such as a colour filter.

In various other embodiments, the detection optical element 506 may be a first colour filter, and the control optical element 508 may be a second colour filter. The detection optical element 506 may be a first optical structure, and the control optical element 508 may be a second optical structure.

In various embodiments, the detection optical element 506 may have an optical property which changes depending on the medium or environment the detection optical element 506 is in contact with. In various embodiments, the control optical element 508 may have an optical property which changes depending on the medium or environment the control optical element 508 is in contact with. The optical property may for instance be the transmittance or the absorbance of optical light passing through the detection optical element 506 or the control optical element 508. In various embodiments, the transmission of optical light through the detection optical element 506 or the control optical element 508 may be based on the optical property of the detection optical element 506 or the control optical element 508.

In various embodiments, the transmission of a first wavelength by an optical element may increase, while the transmittance (or absorbance) of a second wavelength by the optical element may decrease with a specific property, e.g. pH, of the medium or environment the optical element comes into contact with, which may lead to a change in colour. For instance, the transmission of the 400 nm of the optical element may increase with increasing pH, while the transmission of the 600 nm of the optical element may decrease with increasing pH. In various embodiments, the transmission peak or the transmittance peak or the absorbance peak of an optical element may shift with a specific property of the medium the optical element comes into contact with.

In various embodiments, the colour filter may include polyaniline. In various embodiments, the colour filter may include a conjugated polymer or molecule, or an indicator dye. Conjugated polymers may include polyaniline, polythiophene, polypyrrole, poly(phenylene vinylene), poly(ethylenedioxythiophene), poly(azulene), or the like. Indicator dyes may include Gentian violet, Malachite green, Thymol blue, Methyl yellow, Bromophenol blue, Congo red, Methyl orange, Bromocresol green, Methyl red, Methyl purple, Azolitmin, Bromocresol purple, Bromocresol blue, Phenol red, Neutral red, Naphtholphthalein, Cresol red, Cresolphthalein, Phenolphthalein, Thymolphthalein, Alizarine Yellow, Indigo carmine, or the like.

The analyte may be isolated from the control optical element 506 by the control medium. In other words, when the control optical element 506 is in contact with the control medium, the control optical element 506 may be isolated or separated from the analyte.

In various embodiments, the detection sensing element 502 may include a detection photoconductor. The detection photoconductor may include a pair of interdigitated electrodes. The detection photoconductor may include a coating of organic photoconductive material over the pair of interdigitated electrodes. The organic photoconductive material may be or may include poly (3-hexylthiophene):phenyl-C61—butyric acid methyl ester (P3HT: PCBM). In various alternate embodiments, the detection photoconductor may include a coating of (non-organic) photoconductive material such as zinc oxide (ZnO) or titanium oxide (TiO$_x$) over the pair of interdigitated electrodes.

In various embodiments, the control sensing element 504 may include a control photoconductor. The control photoconductor may include a pair of interdigitated electrodes. The control photoconductor may further include a coating of organic photoconductive material over the pair of interdigitated electrodes. The organic photoconductive material may be or may include poly (3-hexylthiophene):phenyl-C61—butyric acid methyl ester (P3HT: PCBM). In various alternate embodiments, the detection photoconductor may include a coating of (non-organic) photoconductive material such as zinc oxide (ZnO) or titanium oxide (TiOx) over the pair of interdigitated electrodes.

Other suitable organic photoconductive materials for the detection photoconductive detector and/or control photoconductive detector may include any one selected from a group consisting of semiconducting polymers or molecules, fullerene derivatives, thiophenes, phthalocyanides, squaraines, azo pigments, and parylene pigments. Other organic photoconductive or photovoltaic materials may include poly[[5-(2-ethylhexyl)-5,6-dihydro-4,6-dioxo-4H-thieno[3,4-c]pyrrole-1,3-diyl][4,8-bis[(2-ethylhexyl)oxy]benzo[1,2-b:4,5-b']dithiophene-2,6-diyl]] (PBDT-TPD), poly({4,8-bis[(2-ethylhexyl)oxy]benzo[1,2-b:4,5-b']dithiophene-2,6-diyl}{3-fluoro-2-[(2-ethylhexyl)carbonyl]thieno[3,4-b]thiophenediyl}) (PTB7), poly[[5-(2-ethylhexyl)-5,6-dihydro-4,6-dioxo-4H-thieno[3,4-c]pyrrole-1,3-diyl](4,4'-didodecyl[2,2'-bithiophene]-5,5'-diyl)] (PBTTPD), poly[N-9'-heptadecanyl-2,7-carbazole-alt-5,5-(4',7'-di-2-thienyl-2',1',3'-benzothiadiazole)] or poly[[9-(1-octylnonyl)-9H-carbazole-2,7-diyl]-2,5-thiophenediyl-2,1,3-benzothiadiazole-4,7-diyl-2,5-thiophenediyl] (PCDTBT), poly[2,6-(4,4-bis-(2-ethylhexyl)-4H-cyclopenta [2,1-b;3,4-b'] dithiophene)-alt-4,7(2,1,3-benzothiadiazole)] (PCP-DTBT), copper(II) phthalocyanine (CuPC), zinc phthalocyanine (ZnPC), or [6, 6]—phenyl C71 butyric acid methyl ester (PC$_{71}$BM).

Other suitable (non-organic) photoconductive materials for the detection photoconductive detector and/or control photoconductive detector may include lead sulfide, selenium, silicon, copper indium gallium selenide/sulfide, cadmium selenide/telluride, copper zinc tin sulfide/selenide etc.

The sensor 500 may further include one or more optical sources configured to generate optical light. The optical source may be a broadband optical source. The optical light may include a plurality of wavelengths.

In various embodiments, the detection optical element 506 may be configured to transmit the first amount of optical light based on a pH of the analyte. In various embodiments, the control optical element 508 may be configured to transmit the second amount of optical light based on a pH of the control medium.

In various embodiments, the sensor 500 may be a printed sensor. The sensor 500 may be printed on a substrate. The sensor 500 or part of the sensor may be printed on a substrate. In various embodiments, the detection photoconductor and/or control photoconductor may be printed. In various embodiments, the detection optical element and/or control optical element may be printed. In various embodiments, the interdigitated electrodes of the detection photoconductor and/or the control photoconductor may be printed, e.g. using conductive ink or a suitable conductive material. In various embodiments, the electrical lines connecting the detection sensing element 502 and the control sensing element 504, and/or the electrical lines connecting the power supply or electrical supply with the detection sensing element 502 and the control sensing element 504 may be printed on the substrate, e.g. using conductive ink or a suitable conductive material.

In various embodiments, the detection sensing element 502 and the control sensing element 504 may act as a voltage divider for colourimetry applications, i.e. sensing relative changes in transmission of light through the detection optical element 506 and the transmission of light through the control optical element 508.

Figure 6:
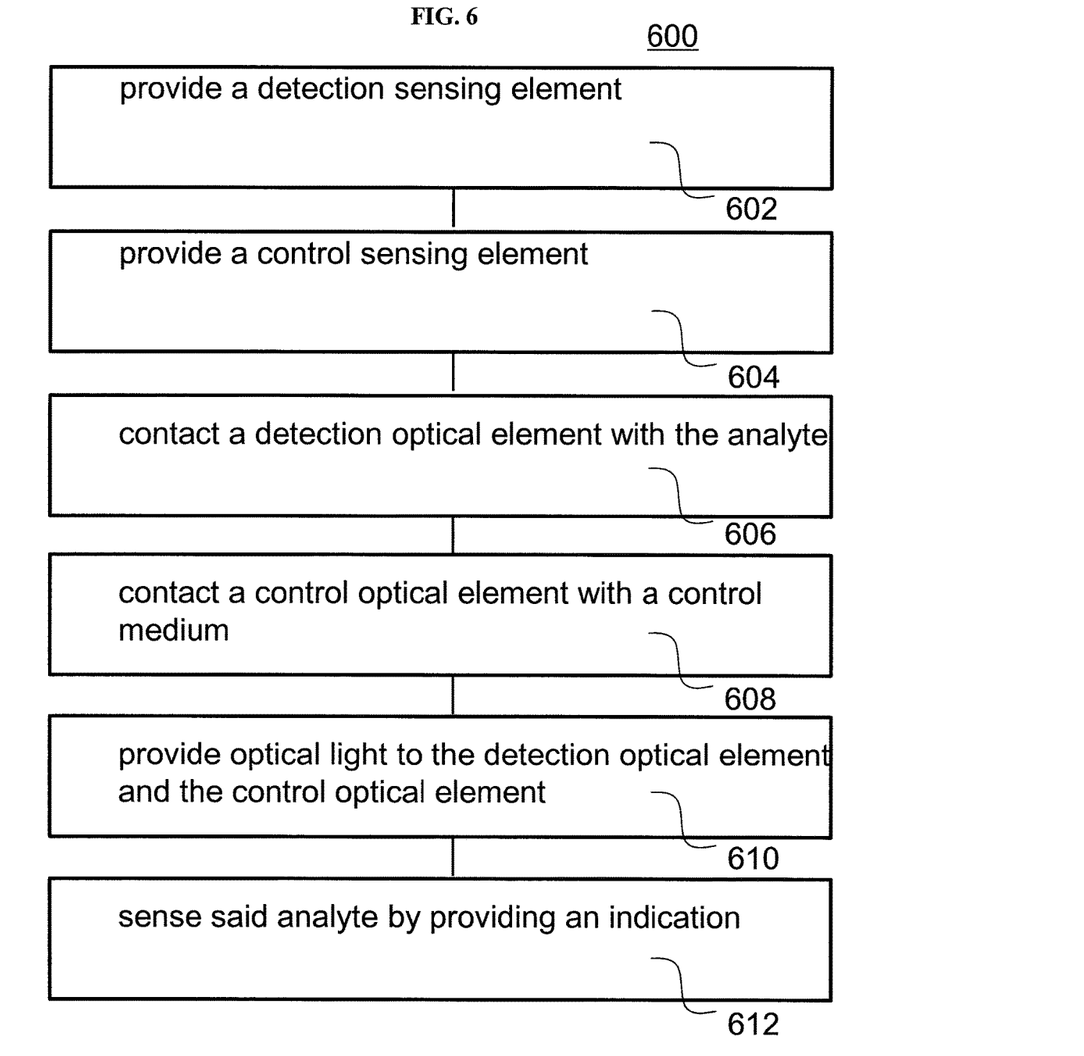
FIG. 6 is a schematic showing a method of sensing an analyte according to various embodiments.

FIG. 6 is a schematic 600 showing a method of sensing an analyte according to various embodiments. The method may include, in 602, providing a detection sensing element having an electrical property variable with the amount of optical light received by the detection sensing element. The method may also include, in 604, providing a control sensing element having an electrical property variable with the amount of optical light received by the control sensing element. The method may also include, in 606, contacting a detection optical element with the analyte. The detection optical element may be configured to transmit a first amount of optical light received by the detection optical element to the detection sensing element when the detection optical element is in contact with the analyte. The method may additionally include, in 608, contacting a control optical element with a control medium, said control optical element configured to transmit a second amount of optical light received by the control optical element to the control sensing element when the control optical element is in contact with the control medium. The method may further include, in 610, providing optical light to the detection optical element and the control optical element so that the detection optical element transmits the first amount of optical light to the detection sensing element and the control optical element transmits the second amount of optical light to the control sensing element. The method may further include, in 612, sensing said analyte based on an indication, the indication based on the electrical property of the detection sensing element when the first amount of optical light is received by the detection sensing element, with respect to the electrical property of the control sensing element when the second amount of optical light is received by the control sensing element.

In other words, sensing the analyte may include providing a detection sensing element and a control sensing element. The detection sensing element and the control sensing element may have an electrical property that changes with amount of optical light received. The method may also include providing a detection optical element and a control optical element. The detection optical element may be used to contact an analyte, while the control optical element may be in contact with a control medium. As the detection optical element and the control optical element are in contact with media of different properties, the amount of optical light transmitted through the detection optical medium (to the detection sensing element) may be different from the amount of optical light transmitted through the control optical medium (to the control sensing element), which may result in a difference between the electrical property of the detection sensing element and the electrical property of the control sensing element. The method may additionally include using an indication based on a relative change in values between the electrical property of the detection sensing element and the electrical property of the control sensing element to sense the analyte.

In various embodiments, sensing the analyte may include providing a measure of the analyte.

The detection optical element may have an optical property, such as transmittance or absorbance, variable based on a property of the medium or environment the detection optical element is in contact with. The control optical element may have an optical property, such as transmittance or absorbance, variable based on a property of the medium or environment the control optical element is in contact with.

In various embodiments, the method may also include providing an optical source to generate the optical light.

In various embodiments, the method may further include electrically connecting a voltage source to the detection sensing element and the control sensing element to generate a voltage potential at a node between the detection sensing element and the control sensing element. In various embodiments, the method may include reading or determining the voltage potential at the node. The indication may be or may refer to the voltage potential at the node. In various embodiments, the method may include connecting a first end of a voltage readout device between the node and an end of the voltage source. The voltage readout may provide a a voltage difference between the node and the end of the voltage source. The indication may be a potential difference between the node and the end of the voltage source.

The indication may provide a measure of the analyte. For instance, the indication may indicate a pH of an analyte. The control optical element may be in contact with a control medium with a fixed pH, e.g. pH 7. In a first experiment, the detection optical element may come into contact with a first analyte of pH 6. In a second separate experiment, the detection optical element may come into contact with a second analyte of pH 3, while the control optical element is still in contact with the control medium of pH 7. The voltage readout may show a first potential difference value for the first experiment, and a second potential difference value for the second experiment. The second potential difference value may be higher than the first potential difference value since the pH difference between the second analyte and the control medium is greater than the pH difference between the first analyte and the control medium.

Figure 7:
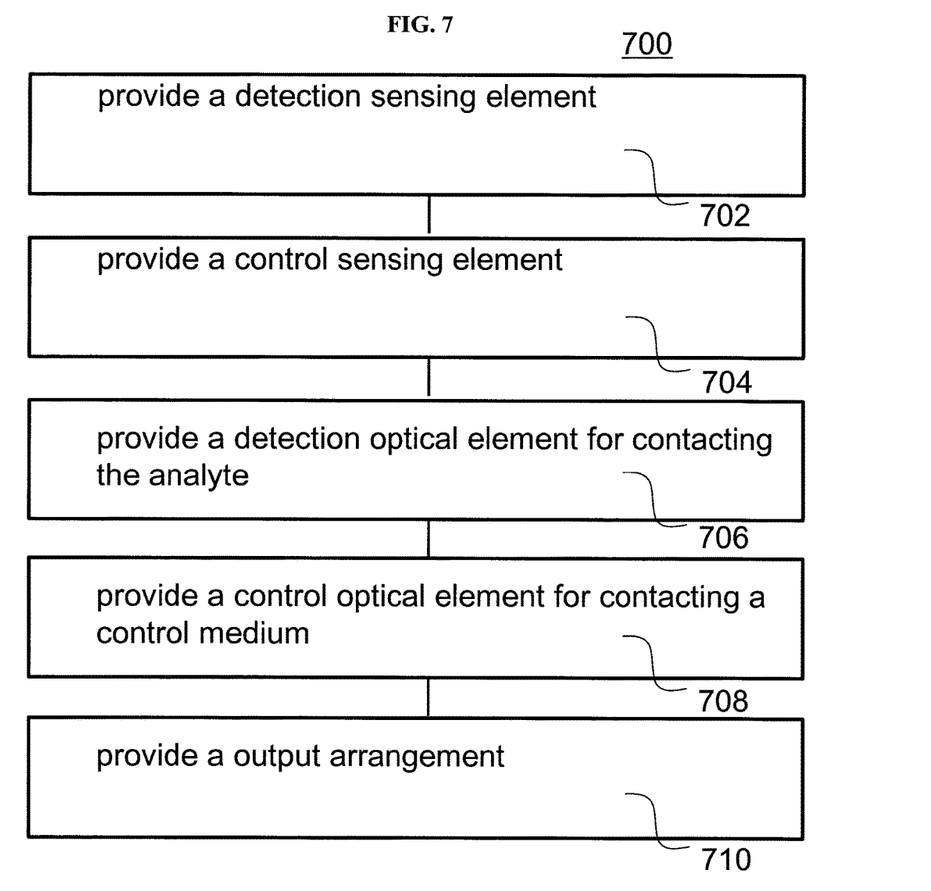
FIG. 7 is a schematic illustrating a method of sensing an analyte according to various embodiments.

FIG. 7 is a schematic 700 illustrating a method of sensing an analyte according to various embodiments. The method may include, in 702, providing a detection sensing element having an electrical property variable with the amount of optical light received by the detection sensing element. The method may include, in 704, providing a control sensing element having an electrical property variable with optical light received by the control sensing element having an electrical property variable with the amount of optical light received by the detection sensing element. The method may also include, in 706, providing a detection optical element for contacting the analyte, said detection optical element configured to transmit a first amount of optical light received by the detection optical element to the detection sensing element when the detection optical element is in contact with the analyte. The method may further include, in 708, providing a control optical element for contacting a control medium, said control optical element configured to transmit a second amount of optical light received by the control optical element to the control sensing element when the control optical element is in contact with the control medium. The method may include, in 710, providing a output arrangement configured to provide an indication based on the electrical property of the detection sensing element when the first amount of optical light is received by the detection sensing element, with respect to the electrical property of the control sensing element when the second amount of optical light is received by the control sensing element, thereby sensing said analyte.

In other words, the method may include providing a detection sensing element and a control sensing element having an electrical property which varies with optical light received. The method may also include providing a detection optical element for contacting an analyte, and a control optical element for contacting a control medium. The detection optical element and the control optical element may be configured to transmit optical light (to the detection sensing element and the control sensing element respectively) based on the medium or environment the detection optical element and the control optical element are in contact with. The method may additionally include providing an output arrangement that provides an indication based on relative changes in values of the electrical property values of the detection sensing element and the control sensing elements, when the detection optical element is in contact with the analyte and the control optical element is in contact with the control medium.

In various embodiments, the method may further include providing a substrate. In various embodiments, the substrate may be a glass substrate, a semiconductor substrate, or a flexible substrate, such as a polymer substrate.

In various embodiments, the detection sensing element may be provided by forming or printing the detection sensing element on the substrate. The control sensing element may be provided by forming or printing the detection sensing element on the substrate.

The method may further include forming or printing the interdigitated electrodes of the detection sensing element on the substrate. The method may further include forming or printing the interdigitated electrodes of the control sensing element on the substrate. The method may further include depositing (e.g. via spincoating) or forming a photoconductive material on or over the interdigitated electrodes of the detection sensing element, and depositing (e.g. via spincoating) or forming a photoconductive material on or over the interdigitated electrodes of the control sensing element. For instance, a suitable conductive material such as indium tin oxide (ITO) may be deposited on the substrate, and the suitable conductive material may be patterned (e.g. using lithography) to form the interdigitated electrodes.

The method may further provide connecting the detection sensing element and the control sensing element. The method may include forming or printing electrical lines to connect the detection sensing element and the control sensing element.

The method may also include providing a power source or an electrical source. The power source and the electrical source may be connected to the detection sensing element and the control sensing element. The method may include forming or printing electrical lines to connect the power source or the electrical source to the detection sensing element and the control sensing element.

The detection optical element may be over the detection sensing element. The control optical element may be on or over the control sensing element. The detection optical element and the control sensing element may be deposited or coated or formed on or over the detection sensing element and the control sensing element respectively. The method may include depositing a continuous optical structure, such as a colour film, on or over the detection sensing element and the control sensing element. The detection optical element may be a first portion of the continuous optical structure and the control optical element may be a second portion of the continuous optical structure. In various embodiments, the continuous optical structure, or the detection optical element and the control sensing element, may be configured to isolate the analyte and/or the control medium from the circuit arrangement, or the detection sensing element and the control sensing element.

The output arrangement may be a readout arrangement or device connected to the detection sensing element and the control sensing element. For instance a voltage readout device may be connected to a node between the detection sensing element and the control sensing element.

Various embodiments may relate to printable colorimetric detectors and a signal amplification design that allows a large, easily-scalable readout voltage signal that is readable by a printed back-end circuit. The signal magnitude may be be tuned with detector design and selection of the photosensitive materials, e.g. ZnO, $TiO_x$, P3HT. Signal magnitudes found in prior arts may be too small for a printable, low-cost back-end circuit. This is technologically significant because various embodiments may be printed on a single flexible substrate together with a back-end circuit and display to create a complete integrated sensing solution with low cost and flexible to be integrated for many applications.

Various embodiments may relate to a printable sensing device that detects change in environment.

The sensing elements may be based on a pair of photoconductors behaving as a voltage divider, which detects change in optical transmission of an analyte-responsive optical filter.

The printable optical filter material may be chosen for application in specific environments, e.g. chemical, biological, physical (temperature, moisture, pressure, strain/stress, etc).

The printable photoconductive material may be chosen to maximize overlap between its optical absorption and the transmission of the optical filter In various embodiments, the chemical environment may be electrically isolated from the electronics. In various embodiments, the sensitivity of the sensor may scale with the drive voltage. In various embodiments, the sensing elements may draw very little or low current from the power source or electrical source.

Experiment

Interdigitated electrodes indium tin oxide (ITO) were patterned by photolithography on glass substrates. The inter-electrode spacing was 20 microns.

P3HT:PCBM was dissolved in 1:1 ratio (by mass) in o-dichlorobenzene and deposited onto the patterned ITO/glass substrates by spin-coating at 500 rpm to form the photoconductive film.

PANI in the form of a commercially-available ink, Panipol, was spin-coated onto a separate, plain glass slide, which formed a green film. Once the PANI film had dried, half of the film was submerged in a pH 9 buffer solution, which turned the film blue. After 2 mins, the buffer solution was blown off, with care taken to avoid contact between the remaining half of the film and the buffer solution.

During measurements, the PANI-coated glass slide was placed on top of the P3HT:PCBM photoconductors so that one photoconductor was covered by green PANI (control), and the other photoconductor covered by blue PANI exposed to the pH 9 buffer solution (test).

Figure 8:
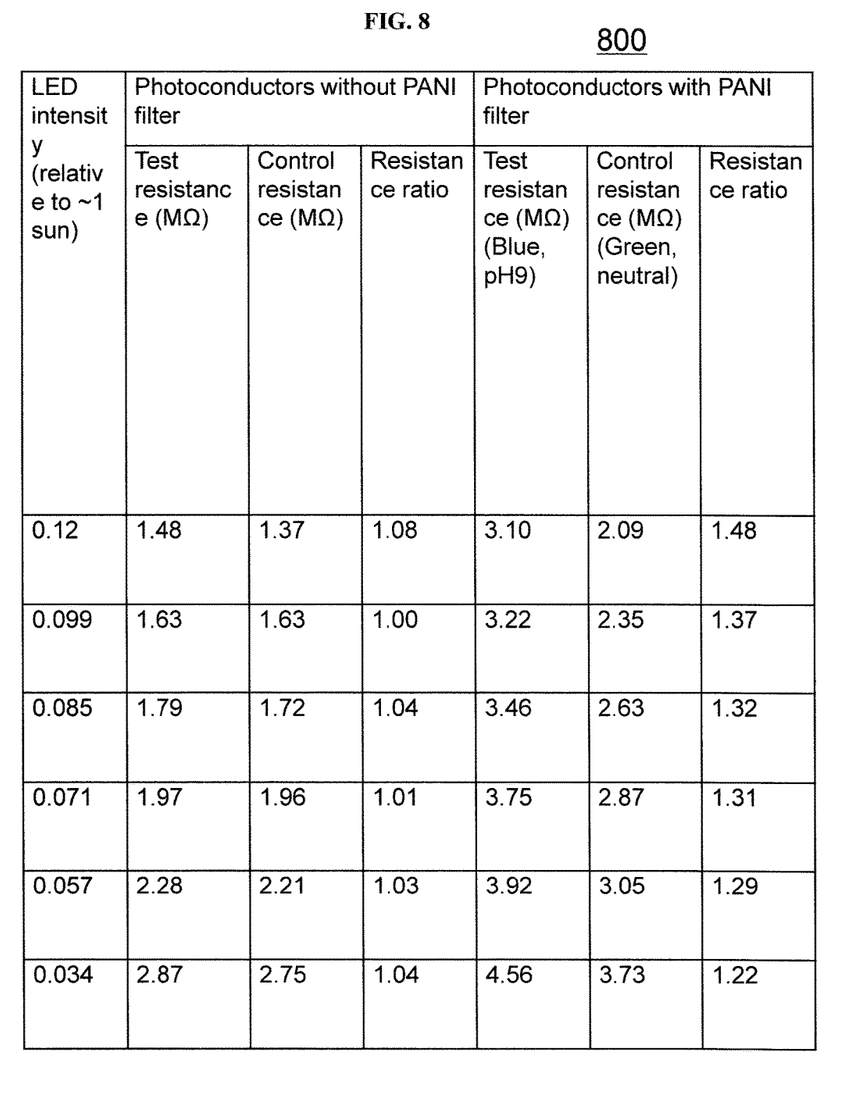
FIG. 8 is a table summarising the resistances of the test and control photoconductors under a white light emitting diode (LED) illumination according to various embodiments.

FIG. 8 is a table 800 summarising the resistances of the test and control photoconductors under a white light emitting diode (LED) illumination according to various embodiments. The illumination intensity is expressed relative to roughly 1-sun intensity.

The resistance ratios of the photoconductors with PANI filters show a similar order of magnitude as those estimated from the preliminary calculations. To give a bearing on the sensitivity of this particular sensor, if this sensor were driven by a 9V battery, the readout voltage would change from 4.5V to 3.6V when the analyte is pH 9, i.e. a change of 0.9V. If the voltage source is changed to a 30V battery, the readout voltage change would be 2.9V.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A sensor for sensing an analyte, the sensor comprising:
a detection sensing element having a resistance variable with an amount of optical light received by the detection sensing element;
a control sensing element having a resistance variable with an amount of optical light received by the control sensing element;
a detection optical element for contacting the analyte, said detection optical element configured to transmit a first amount of optical light received by the detection optical element to the detection sensing element when the detection optical element is in contact with the analyte;
a control optical element for contacting a control medium, said control optical element configured to transmit a second amount of optical light received by the control optical element to the control sensing element when the control optical element is in contact with the control medium;
a voltage source in electrical connection with the detection sensing element and the control sensing element, the voltage source configured to generate a voltage potential at a node between the detection sensing element and the control sensing element, the voltage potential at the node based on a ratio of a potential difference across the detection sensing element and the potential difference across the control sensing element; and
a voltage readout device configured to measure the voltage potential of the node based on the resistance of the detection sensing element when the first amount of optical light is received by the detection sensing element, with respect to the resistance of the control sensing element when the second amount of optical light is received by the control sensing element, thereby sensing said analyte.

2. The sensor according to claim 1, wherein the detection sensing element and the control sensing element are connected in series.

3. The sensor according to claim 1, wherein the detection optical element is a first portion of a colour filter and the control optical element is a second portion of the colour filter; and wherein the first portion of the colour filter covers the detection sensing element and the second portion of the colour filter covers the control sensing element.

4. The sensor according to claim 3, wherein the colour filter comprises a conjugated polymer or molecule, or an indicator dye.

5. The sensor system according to claim 1, wherein the analyte is isolated from the control optical element by the control medium.

6. The sensor according to claim 1, wherein the detection sensing element comprises a detection photoconductor; and wherein the control sensing element comprises a control photoconductor.

7. The sensor according to claim 6, wherein the detection photoconductor comprises a pair of interdigitated electrodes and a coating of organic photoconductive material over the pair of interdigitated electrodes.

8. The sensor according to claim 7, wherein the organic photoconductive material is any one selected from a group consisting of fullerene derivatives, semiconducting polymers or molecules, thiophenes, phthalocyanides, squaraines, azo pigments, and parylene pigments.

9. The sensor according to claim 6, wherein the control photoconductor comprises a pair of interdigitated electrodes and a coating of organic photoconductive material over the pair of interdigitated electrodes.

10. The sensor according to claim 9, wherein the organic photoconductive material is any one selected from a group consisting of fullerene derivatives, semiconducting polymers or molecules, thiophenes, phthalocyanides, squaraines, azo pigments, and parylene pigments.

11. The sensor according to claim 1, further comprising: an optical source configured to generate optical light.

12. The sensor according to claim 1, wherein the detection optical element is configured to transmit the first amount of optical light based on a pH of the analyte; and wherein the control optical element is configured to transmit the second amount of optical light based on a pH of the control medium.

13. The sensor according to claim 1, wherein said sensor is a printed sensor.

14. A method of sensing an analyte, the method comprising:
providing a detection sensing element having a resistance variable with an amount of optical light received by the detection sensing element;
providing a control sensing element having a resistance variable with an amount of optical light received by the control sensing element;
electrically connecting a voltage source to the detection sensing element and the control sensing element, the voltage source configured to generate a voltage potential at a node between the detection sensing element and the control sensing element, the voltage potential at the node based on a ratio of a potential difference across the detection sensing element and the potential difference across the control sensing element;

contacting a detection optical element with the analyte, said detection optical element configured to transmit a first amount of optical light received by the detection optical element to the detection sensing element when the detection optical element is in contact with the analyte;

contacting a control optical element with a control medium, said control optical element configured to transmit a second amount of optical light received by the control optical element to the control sensing element when the control optical element is in contact with the control medium;

providing optical light to the detection optical element and the control optical element so that the detection optical element transmits the first amount of optical light to the detection sensing element and the control optical element transmits the second amount of optical light to the control sensing element; and sensing said analyte by measuring the voltage potential of the node, the voltage potential of the node based on the resistance of the detection sensing element when the first amount of optical light is received by the detection sensing element, with respect to the resistance of the control sensing element when the second amount of optical light is received by the control sensing element.

15. The method according to claim 14, further comprising:

providing an optical source to generate the optical light.

16. A method of fabricating a sensor for sensing an analyte, the method comprising:

providing a detection sensing element having a resistance variable with an amount of optical light received by the detection sensing element;

providing a control sensing element having a resistance variable with an amount of optical light received by the control sensing element;

providing a detection optical element for contacting the analyte, said detection optical element configured to transmit a first amount of optical light received by the detection optical element to the detection sensing element when the detection optical element is in contact with the analyte;

providing a control optical element for contacting a control medium, said control optical element configured to transmit a second amount of optical light received by the control optical element to the control sensing element when the control optical element is in contact with the control medium;

providing a voltage source in electrical connection with the detection sensing element and the control sensing element, the voltage source configured to generate a voltage potential at a node between the detection sensing element and the control sensing element, the voltage potential at the node based on a ratio of a potential difference across the detection sensing element and the potential difference across the control sensing element; and providing a voltage readout device configured to measure the voltage potential of the node based on the resistance of the detection sensing element when the first amount of optical light is received by the detection sensing element, with respect to the resistance of the control sensing element when the second amount of optical light is received by the control sensing element, thereby sensing said analyte.

\* \* \* \* \*